United States Patent
Yoshida et al.

(10) Patent No.: US 6,485,721 B1
(45) Date of Patent: *Nov. 26, 2002

(54) BIOLOGICALLY ACTIVE SUBSTANCE-SECRETING HYBRID GEL

(75) Inventors: Susumu Yoshida, Hiroshima (JP); R. Andrew Cuthbertson, San Francisco, CA (US); Katsutoshi Yoshizato, Hiroshima (JP)

(73) Assignees: Research Development Corporation of Japan, Saitama (JP); Genentech, Inc., San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/428,822

(22) Filed: Apr. 25, 1995

(30) Foreign Application Priority Data

Apr. 25, 1994 (JP) .............................. 94-86979
Nov. 22, 1994 (JP) ........................... 94-288487

(51) Int. Cl.⁷ .......................... A01N 63/00; A61F 2/00; C12N 15/00; C12N 5/08
(52) U.S. Cl. .................. 424/93.21; 424/93.2; 424/423; 424/424; 435/320.1; 435/455; 435/360; 435/371
(58) Field of Search .............................. 424/486, 93.21, 424/93.1, 93.2, 422, 423, 424; 514/44; 435/320.1, 325, 360, 371, 455

(56) References Cited

U.S. PATENT DOCUMENTS 4,485,096 A * 11/1984 Bell .............................. 424/95
5,219,740 A * 6/1993 Miller et al. ............... 435/69.6

OTHER PUBLICATIONS

Bell et al. Science. 211:1052–4, Mar. 1981.*
Yoshida et al. Tissue Engineering. 3(3): 243–255, 1997.*
Kawakami et al., Somatic Gene Therapy for Diabetes With an Immunological Safety System for Complete Removal of Transplanted Cells. Diabetes, vol. 41, pp. 956–961, Aug. 1992.*
Hull et al., Structural Integration of Skin Equivalents Grafted to Lewis and Sprague–Dawley Rats. Journal of Investigative Dermatology, vol. 81, pp. 429–436, 1983.*
Hull et al. Coverage of full–thickness burns with bilayered skin equivalents: A preliminary clinical trial. Surgery, vol. 107, No. 5, pp. 496–502, May 1990.*
Orkin et al., NIH Gene Therapy Meeting Report, Dec. 7, 1995.*
Taniguchi et al., Tranplantation Proceedings, 24(6):2977–2978, Dec. 1992.*
Kawakami et al., Diabetes, 41:956–96, Aug. 1992.*
Yoshizato et al., Chemical Abstracts, vol. 120,#226909, 1994.*
Nishikawa et al., Chemical Abstracts, vol. 107,#131718, 1987.*

* cited by examiner

Primary Examiner—Scott D. Priebe
Assistant Examiner—Shin-Lin Chen
(74) Attorney, Agent, or Firm—Wenderoth, Lind & Ponack, L.L.P.

(57) ABSTRACT

The present invention provides a biologically active substance secreting hybrid gel, which consists essentially of a biopolymeric gel and cells containing an expression vector with a gene encoding the biologically active substance to produce the substance. According to the present invention, it is possible to develop a gene therapy by skin transplantation allowing stable drug medication for a long time; alleviating pains of patients; and allowing fine adjustment of the dosage and control of genes externally without using retrovirus-derived vector that tend to invoke the risk of mutation to wild types as in the conventional prescription.

7 Claims, No Drawings

BIOLOGICALLY ACTIVE SUBSTANCE-SECRETING HYBRID GEL

BACKGROUND OF THE INVENTION

1. Field of the Invention

The present invention relates to biologically active substance-secreting hybrid gel. More particularly, the present invention relates to a new hybrid gel which secrets a biologically active substance, and is useful as an external-use prescription such as an artificial skin used in the treatment of various difficult-to-cure diseases requiring long-term and continuous medication of physiological active substances in order to maintain biological functions.

2. Description of Related Art

Three methods are available to cure diseases which are caused by the loss or decrease in the functions of human cells for any reason. Namely, the lost or decreased functions are compensated for by
1) drug medication,
2) transplantation of organs/tissues or cells, or
3) gene therapy Insulin dependent diabetes mellitus, for example, is caused by the destruction of the β-cells, which produce insulin having the function of reducing the blood sugar level, and which occur in the islets of Langerhans of the pancreas. Patients who suffer from insulin dependent diabetes mellitus have a high blood sugar level, and as a result, the concentration of sugar in their urine increases. When the blood sugar level remains high, the functions of various human cells are damaged, causing serious complications.

It is thus necessary to externally dispense insulin and control the blood sugar level in order to cure the insulin dependent diabetes mellitus patients. Insulin dependent diabetics must have insulin doses administered several times every day for life. This is a serious physical and mental agony to the patient, and in addition, self-medication always involve risk of life because of possible mis-dispensing.

One of alternative methods to self-medication of insulin in transplantation of the pancreas or the islets of Langerhans (K. Kubota and Y. Idezuki, Nippon Rinsho: in Japanese, 48:1052, 1990). However, this treatment has a number of problems, such as, for example, few donors, difficulty of controlling immunorejection caused by the transplanted pancreas or the tissues, complicated surgical operations for transplantation requiring techniques of a high level, and hazards involved in the operation.

Gene therapy is one of the most exciting medical technique to being employed solve the above problems, and various gene therapies are being clinically tested for treating patients having serious diseases in the United States and other countries in the 1990s (N. K. Summers, Biotechnology 12;42, 1994). A method of treating diabetes based on the above technique has been proposed (R. F. Selden et al, The New England Journal of Medicine, 317(17): 1067, 1987). In this particular method, and insulin gene is introduced into culture cells, and the cells are transplanted to the body of the patient in order to assure continuous secretion of insulin produced by the introduced gene. This method has a number of problems such as, for example, difficulty of controlling secretion of insulin from the transplanted insulin producing cells and inability of removing the transplanted cells later from the body. It is generally known that the gene therapy is a promising and advanced medical technique for not only insulin dependent diabetes mellitus and genetic diseases such as serious immune deficiency diseases but also cancer, AIDS, and other hard-to-cure diseases. For this reason, many approaches have been proposed and gene therapy is actually being conducted in practical clinical cases. Most of these gene therapies use retrovirus-derived vectors to introduce genes into the cells utilizing cell infection of the virus.

This technique to use retrovirus-derived vectors has the drawback that the effectiveness of gene introduction depends on the affinity of the virus to the cells, and there is a possibility that the deactivated virus vectors will transform into wild retroviruses. In addition, conventional gene therapy generally has a problem in there being difficulty of controlling the introduced genes externally.

SUMMARY OF THE INVENTION

The present invention intends to provide a new art of transplanting cells containing a gene which encodes biologically active substance into the skin and controlling the expression of the gene externally. More specifically, the present invention intends to solve the problems of the prior art by transplanting biologically active substance-producing cells to the skin of a human body as a hybrid gel (cell-incorporating gel).

The present invention provides a biologically active substance-secreting hybrid gel, which consists of biologically active substance-producing cells and a biopolymeric gel.

In the case of said hybrid gel, a preferable embodiment is that the biologically active substance-producing cells are enclosed in or laminated on the biopolymeric gel, or laminated on the biopolymeric gel enclosing the biologically active substance-producing cells.

The present invention also provides a biologically active substance-secreting hybrid gel, which consists of biologically active substance-producing cells, animal skin cells and biopolymeric gel.

In the case of said hybrid gel, a preferable embodiment is that the animal skin cells are laminated on the biopolymeric gel enclosing the biologically active substance-producing cells; the biologically active substance-producing cells are laminated on the biopolymeric gel enclosing the animal skin cells; the animal skin cells and the biologically active substance-producing cells are laminated on the biopolymeric gel; or the animal skin cells or the biologically active substance-producing cells are laminated on the biopolymeric gel enclosing the animal skin cells and the biologically active substance-producing cells.

Furthermore, in the case of the biologically active substance-producing cells being enclosed in the biopolymeric gel, said cells are enclosed together with meshy material or porous membrane.

In the present invention, moreover, the biologically active substance-producing cells may be skin cells (i.e., skin fibroblasts or skin epidermal cells) which contain an expression vector recombinant with a DNA sequence encoding the biologically active substance such as insulin. And, said expression vector may be plasmid vector pBMG-neo-ins possessing insulin CDNA and neomycin resistance gene, or plasmid vector pRIS-proins-Ifur-IIfur-B10D which possesses mutant insulin gene expressing stable insulin by the action of furin.

According to the present invention, it will be possible to develop a gene therapy by skin transplantation allowing stable drug medication for a long time; alleviating pains of the patients; and allowing fine adjustment of the dosage and control of gene externally without using retrovirus-derived vectors that tend to invoke the risk of mutation to wild types as in the conventional technique.

DETAILED DESCRIPTION OF THE INVENTION

The cells used in the invention are enclosed in or laminated on the biopolymeric gel of the present invention and produce a biologically native substance necessary for or deficient in the body, and the substance is continually secreted into the body. The production of biologically active substance is increased when meshy material or porous membrace, etc. are enclosed in the gel together with the biologically active substance producing cells. Thus the hybrid gel of the present invention can be effectively used as, for example, an external-use prescription such as an artificial skin. The gene expressing biologically active substance is introduced to the cells by, for example, plasmid vector, and thus, unlike conventional gene therapy, no risk of conversion into wild retro-viruses owing to the retrovirus-derived vectors is involved. In addition, the introduced gene can be easily controlled externally because the gene-containing cells are transplanted to the skin.

The following functions are available in concrete:

1) After transplantation, the biologically active substance is dispensed for a long time stably without the knowledge of the patient. This dramatically reduces the physical and mental agony of the patient subject to repeated medication in the conventional treatment.
2) A very simple surgery is used to transplant or remove the hybrid gel of the present invention from the skin. For this reason, the quantity of artificial skin to be transplanted can be adjusted at any time freely while watching the process condition of the treatment, It is thus easy to determine optimum conditions for treatment.
3) The rate of substance secretion from the cells in or on the gel can be controlled by means of inducible promoters to control biological expression of the DNA sequence encoding the biologically active substance and various induction stimuli (hormones, heavy metals, temperature, etc.) applied to the transplanted artificial skin. This allows fine adjustment of the substance secretion rate.
4) The transplanted cells are enclosed in or on the gel and thus are hardly affected by immunorejection of the patient. It is thus possible to decrease the quantity of immunosuppressants generally used in the transplantation of tissues in the conventional technique. The risk of side effects owing to the use of immunosuppressants is thus greatly reduced. Of course there is no problem of immunorejection if the cells of the patient himself are used in the gene therapy because such therapy is a self-transplantation.
5) Simple operation without the need of the patient's hospitalization is safe and free from the risk incurred in conventional treatment. Because this is a transplantation to the skin, the condition of transplantation is visible externally at all times. The transplanted artificial skin can be removed when necessary.

Various biologically active substance-producing cells can be used in the present invention for incorporating expression vector with gene therefor in the cells. For example, insulin-producing cells can be prepared by transfecting placmid vector pBMG-neo-ins possessing cDNA of insulin and neomycin resistance gene (selection marker) to animal cells using a known method. Another method is to transfect plasmid vector pRIS-proins-Ifur-IIfur-B10D into animal cells. This plasmid vector contains mutant insulin gene that convert proinsulin expressed from the gene into insulin by the action of furin and by the substitution of the 10th amino acid in the insulin chain B.

The gel to accommodate the biologically active substance-producing cells may be prepared from, for example, collagen, fibrin, agarose, etc. by using known methods. For example, the hybrid gel containing cells with insulin genes therein may be prepared and used as artificial skin for curing diabetics in the following manner:

(1) Pieces of skin of an experimental animal are collected. Epidermal cells and fibroblasts, two major constituent cells of skin, are separated from the skin samples and cultured.
(2) Expression vector containing insulin gene is transduced into these cells to derive insulin-secreting cell lines.
(3) Hybrid type artificial skin with the insulin-secreting function is constructed from these cell lines using collagen gels, etc.
(4) The insulin-secreting hybrid type artificial skin is transplanted.

To be more specific, the hybrid gel secreting biologically active substance of the present invention can be manufactured in accordance with the method of Asaga et al (H. Asaga et al, Experimental Cell Research, 193: 167, 1991) as follows:

Quadruple concentrated medium of cell culture, serum, purified water, and, for example, collagen (0.5% solution) are mixed in the ratio of 2.5:1:2.5:4 according to the required quantity while cooling the mixture with ice. An aqueous solution of 1N sodium hydroxide is mixed dropwise into the mixture to adjust to pH 7.4. The mixture is separately injected into hydrophobic plastic laboratory dishes of 35 mm in diameter, 2 ml in each dish. The dishes are immediately transferred to a 37° C. thermostat. The collagen solidifies in several minutes to produce gel. Biologically active substance-producing cells are mixed into the above mixture just before collagen solidifies in order to enclose the cells in the gel.

To allow meshy material or porous membrane to coexist in the gel, one needs only to mix these in the above solution together with the biologically active substance-producing cells.

Commercially available culture solutions, serum and collagen can be used in the present invention.

It is effective to give an appropriate strength to the collagen gels to facilitate transplantation of the product to the skin. An appropriate strength can be given to the gel by, for example, mixing an appropriate number of skin-derived fibroblasts according to the method of Bell et al (E. Bell et al, Proceedings of the National Academy of Sciences, 76(3): 1274, 1979). An appropriate strength can be given to the gel as a result of contraction of the gel owing to the fibroblasts. Skin-derived fibroblasts can be obtained, for example, by culturing a small portion of skin collected from the patient according to the primary explant technique (R. I. Freshrey, Culture of Animal Cells, Alan R. Liss, Inc., New York, 1987).

It is also effective to make the gel surface active to ensure good attachment to the skin by overlaying by culture skin-derived epidermal cells on the gel before they are transplanted to the skin.

Skin-derived epidermal cells to be overlaid on the gel may be obtained by culturing epidermal cells obtained from the skin of the patient himself in the same way as described for the fibroblasts using the method of, for example, Green et al (H. Green et al, Proceedings of the National Academy of Sciences 76: 5665, 1979).

It goes without saying that the present invention is effective also when the gel is transplanted subcutaneously without overlaying epidermal cells.

Practically, many forms are of the invention available.

EXAMPLES

Examples are shown below to further describe the present invention in detail. These examples should not be construed as limiting.

Example 1

Hybrid gel (or simply Gel hereafter) of the present invention were prepared to evaluate the method of medication and their application to the treatment of diabetics by conducting in-vitro experiments and in-vivo experiments with animal diabetic models as described below.

In-vitro Experiment

Gel containing proinsulin-producing cells were cultured, and proinsuline secreted into the culture medium were measured.

1) Materials

Three types of skin-derived cell lines were used.
(1) Mouse embryo fibroblasts (NIH3TS3)
(2) Rat skin fibroblasts containing insulin gene (RSFins)
(3) Rat skin epidermal cells containing insulin gene (RSKins)

RSFins and RSKins were prepared by transduction of insulin gene (G. I. Bell et al, Nature, 284 (6):26, ;1980) into fibroblasts (RSF) and epidermal cells (RFK), respectively, which were obtained from the primary culture of rat skin. Insulin gene was transfected into the fibroblasts and epidermal cells using plasmid vector pBMG-neo-inS which possesses human insulin cDNA. The vector pBMG-neo-ins was made according to the following method of (Y. Kawakami et al, Diabetes 41: 956, 1992. A 518-bp DNA fragment digested with NcoI and BamHI was prepared from a human preproinsulin plasmid. This fragment included a 330-bp coding sequence, a 73-bp 3' untranslated sequence, and a 115-bp genomic sequence. This fragment was subcloned into the XhoI cloning site of the pBMGNeo expression vector, of which a detailed structure has been previously reported in Karasuyama et al. Eur. J. Immunol., 18: 97–104 (1988), by blunt-end ligation to produce pBMG-Neo-Ins. The insulin gene was then transfected according to the method of Chen and Okayama (C. Chen and H. Okayama, Molecular and Cellular Biology 7(8): 2745, 1987) The vector-containing cells were then selectively increased in culture media of G418 of 400 $\mu$g/ml concentration.

These cells had no processing enzymes to insulin and thus secreted proinsulin, precursor of insulin. It should be noted that proinsulin also has the functions of insulin (S. N. Davis et al., Journal of Clinical Endocrinogy and Metabolism, 75 (6): 1282–1285, 1992).

2) Culture Medium

The culture medium for RSFins consisted of Dulbecco's modified Eagle's medium (Gibco, Grand Island, N.Y.), to which fetal bovine serum (HyClone, Logan, Utah) was added to the ratio of 10% (medium A).

The culture medium for RSKins consisted of a 7:3 mixture of Dulbecco's modified Eagle's medium and MCDB152 medium (Kyokuto, Tokyo), to which hydrocortisone (0.4 $\mu$g/ml), insulin (5 $\mu$g/ml), transferrin (5 $\mu$g/ml), triiodothyronine (2 nM), cholera toxin (0.1 nM), adenine (100 $\mu$M) and fetal bovrine serum (10%) were added (medium B).

The cells were enclosed in and/or laminated on the gel. The resultant hybrid gel was cultured in medium A.

3) Procedures $5\times10^5$ cells of RSFins each were enclosed in the gel and laminated on another gel to prepare Gels A and B, respectively. Gels C and D were further prepared by placing $5\times10^5$ cells of RSKins each in and on the gels, respectively. NIH3T3 cells of the same number were enclosed in Gels C and D to give contractive function. The structure of these Gels is summarized in Table 1. These cells were cultured at 37° C. One day after the preparation, 2 ml culture medium was added to continue culture. Thereafter, the culture medium was replaced with fresh medium every other day. The retrieved culture medium was frozen for storage, melted when necessary, and measured for proinsulin concentration in the culture medium. Proinsulin concentration was measured as a value of immunoreactive insulin (IRI) using the EIA kit (Sanko Junyaku, Tokyo).

TABLE 1

| Gel | Cells in the gel | Cells on the gel |
| --- | --- | --- |
| Gel A | RSFins (N = 5 × 10$^5$) | None |
| Gel B | None | RSFins (N = 5 × 10$^5$) |
| Gel C | RSKins (N = 5 × 10$^5$)<br>NIH3T3 (N = 5 × 10$^5$) | None |
| Gel D | NIH3T3 (N = 5 × 10$^5$) | RSKins (N = 5 × 10$^5$) |

4) Results

The results of this experiment are shown in Table 2. Both of the cell lines enclosed in and laminated on the gel secreted a stable quantity of proinsulins into the culture medium for 25 culture days. It is thus possible to deliver proinsulins into the body when these Gels are transplanted to the skin.

TABLE 2

Secretion of proinsulins from Gels to culture medium ($\mu$U/ml/day)

| | Days of culture | | | |
| --- | --- | --- | --- | --- |
| Gel | 4 days | 8 days | 14 days | 24 days |
| Gel A | 252 | 248 | 340 | 399 |
| Gel B | 239 | 255 | 350 | 325 |
| Gel C | 201 | 215 | 340 | 363 |
| Gel D | 210 | 212 | 340 | 328 |

In-vivo Experiment 1

Proinsulin producing cell-enclosed hybrid gels were transplanted to model diabetic animals to evaluate the curing effects by measuring blood sugar level.

1) Experiment Animals 200 mg/kg streptozotocin (Sigma, St.Louis, Mo.) was intraperitoneally administered to the Balb/c nude mice (5-weeks old, male) at three times in four days to induce a diabetic condition. The mice were used for experiments when they were 7 weeks old.

2) Materials

Three types of rat skin-derived cell lines were used.
(1) RSF
(2) RsFins
(3) RSKins 3) Method for Preparing Gels $5\times10^5$ cells of RSFins were enclosed in collagen gel and RSKins cells of the same number were laminated on the surface of said gel to preparer Gel E. $5\times10^5$ cells of RSF were enclosed in collagen gel and RSKins cells of the same number were laminated on the surface of said gel to preparer Gel F. The structure of these Gels is summarized in Table 3. These cells were cultured for six days at 37° C. and then used for transplantation. Gels E and F produced proinsulins 484 and 404 μIU/day, respectively.

TABLE 3

| Gel | Cells in the Gel | Cells on the gel |
| --- | --- | --- |
| Gel E | RSFins (N = 5 × 10$^5$) | RSKins (N = 5 × 10$^5$) |
| Gel F | RSF (N = 5 × 10$^5$) | RSKins (N = 5 × 10$^5$) |

3) Procedures

The skin of two of the above model diabetic animals was cut away in the area of approximately 25 and 200 mm square, respectively, and Gels E and F, cultured for six days after preparation, were cut and transplanted to the full naked area (cut Gel weight was 24 and 191 mg by wet weight, respectively). After transplantation, about 20 μl blood was collected from the tail of the animals (ID Nos. 3 and 4) every other day to measure the blood sugar level. Two non-transplanted diabetic animals (ID Nos. 1 and 2) were used for control. The blood sugar level was measured using glucose CII test (Wako Pure Chemical Industry, Osaka).

4) Results

The results of this experiment are shown in Table 4. The control animals show a continuous rise in the blood sugar level while such a rise in the blood sugar level is suppressed and a tendency of decreasing blood sugar level is indicated in the Gel-transplanted animals.

TABLE 4

Effect of Gel transplantation to diabetic mouse

| | | Blood sugar level (mg/dl) | | |
| --- | --- | --- | --- | --- |
| | | Before | After dosing STZ | |
| Experiment group | ID No. | dosing STZ 2 hours before dosing STZ | 10th day after dosing STZ (1 day before gel transplantation) | 5th day after gel transplantation |
| Control group | 1 | 108 | 380 | 557 |
| | 2 | 113 | 415 | 511 |
| Gel transplanted group | 3 | 90 | 489 | 437 |
| | 4 | 88 | 392 | 331 |

Note: STZ = Streptozotocin

In-vivo Experiment 2

Proinsulin producing cell-enclosed hybrid gels were transplanted to model diabetic animals to evaluate the curing effects by measuring blood sugar lebel and body weight of the animals.

1) Experimental Animals 200 mg/kg of streptozotocin (Sigma) was intraperitoneally administered to the Bulb/c nude mice (7-weeks old, male) at each two days to induce the diabetic condition. The transplantation of hybrid gel was conducted after two days of the administration of streptozotocin.

2) Materials

Three types of rat skin-derived cell lines were used.
(1) RSF
(2) RSFins
(3) RSK 3) Method for Preparing Gels 10$^6$ cells of RSFins were enclosed in collagen gel and RSK cells of the same number wGre laminated on the surface of said gel to prepare Gel M. 10$^6$ cells of RSK were enclosed in collagen gel and RSFins cells of the same number were laminated on said gel to prepare Gel N. The structure of these Gels is summarized in Table 5. These cells were cultured for 7 days at 37° C. and then used for transplantation. Gels M and N produced proinsulin 300.8 and 1.5 μIU/hour, respectively.

TABLE 5

| Gel | Cells in the gel | Cells on the gel |
| --- | --- | --- |
| Gel M | RSFins (N = 10$^6$) | RSK (N = 10$^6$) |
| Gel N | RSF (N = 10$^6$) | RSK (N = 10$^6$) |

4) Procedures

The skin at right side abdomen of three animals was cut away in the form of a circle of B-10 mm diameter, and Gel M, cultured for 7 days after preparation was transplanted for the naked area. After tranplantation, about 5 μl blood was collected from the tail of the animal every other day to measure the blood sugar level. The body weight of the animals were also measured every other day. Remaining three animals to which Gel N was transplanted in a same manner were used for control. The blood sugar level was measured using Gultest-E (Sanwa Chemical Institute, Nagoya, Japan).

5) Results

The results of this experiment were shown in Table 6. The Gel N-transplanted animals show a continuous rise in the blood sugar level while such a rise in level is suppressd in the Gel M-transplanted group. The Gel M group showed an inhibitory effect on decrease of body weight as shown in the Gel N group during the course of the experiment.

TABLE 6

Effects of Gel transpalntaion to diabetic mouse

| Days before/after transplantation | Body Weight (B.W: upper: g) and Blood Sugar Level (B.S.L: lower: mg/dl) | | | | | | | | | | |
| --- | --- | --- | --- | --- | --- | --- | --- | --- | --- | --- | --- |
| | −3 | −1 | 3 | 5 | 7 | 9 | 11 | 13 | 15 | 17 | 19 |
| Gel N-Group (control) | 24.7 | 23.3 | 18.2 | 17.9 | 14.8 | 17.9 | 17.7 | 17.0 | 15.9 | 15.7 | 15.7 |
| | 92 | 251 | 258 | 315 | 394 | >500 | >500 | >500 | >500 | 384 | >500 |
| | 21.0 | 20.2 | 16.9 | 17.2 | 14.3 | 17.0 | 16.6 | 16.6 | 15.8 | 16.8 | 16.9 |
| | 116 | 224 | 193 | 337 | 320 | 453 | 340 | >500 | >500 | 494 | 423 |
| | 22.1 | 20.4 | 15.4 | 14.8 | 12.8 | 14.6 | 13.5 | 13.5 | 13.2 | 12.1 | NT |
| | 97 | 268 | 222 | 274 | >500 | >500 | 330 | >500 | >500 | >500 | NT |
| Ave. of B.W. = | 22.6 | 21.3 | 16.8 | 16.6 | 14.0 | 16.5 | 15.9 | 15.7 | 15.0 | 14.9 | 16.3 |
| Ave. of B.S.L = | 102 | 248 | 224 | 309 | >405 | >484 | >390 | >500 | >500 | >459 | >462 |
| Gel M-Group | 22.2 | 20.8 | 17.4 | 17.5 | 17.1 | 17.5 | 18.1 | 18.2 | 18.8 | 17.6 | 18.4 |
| | 140 | 217 | 109 | 290 | 471 | >500 | 389 | 372 | >500 | 388 | >500 |

TABLE 6-continued

Effects of Gel transpalntaion to diabetic mouse

| Days before/after transplantation | Body Weight (B.W: upper: g) and Blood Sugar Level (B.S.L: lower: mg/dl) | | | | | | | | | | |
|---|---|---|---|---|---|---|---|---|---|---|---|
| | −3 | −1 | 3 | 5 | 7 | 9 | 11 | 13 | 15 | 17 | 19 |
| | 22.3 | 21.8 | 17.7 | 17.1 | 18.5 | 18.4 | 19.3 | 19.9 | 20.6 | 20.6 | 20.6 |
| | 97 | 206 | 172 | 295 | 415 | 442 | 345 | 403 | >500 | 413 | 401 |
| | 20.7 | 20.2 | 18.6 | 18.5 | 16.8 | 16.5 | 17.5 | 18.1 | 18.6 | 19.0 | 18.4 |
| | 127 | 296 | 137 | 197 | 335 | 423 | 314 | 369 | 443 | >500 | 443 |
| Ave. of B.W. = | 21.7 | 20.9 | 17.9 | 17.7 | 17.5 | 17.5 | 18.3 | 18.7 | 19.3 | 19.1 | 19.1 |
| Ave. of B.S.L = | 121 | 240 | 139 | 261 | 407 | >455 | 349 | 381 | >481 | >434 | >448 |

Note)
TN indicates non-testable cases because of the death of subject.

Example 2

Another form of hybrid gel of the present invention was prepared and the effects were evaluated using in-vitro experiment and in-vivo experiment on diabetic-model animals as described below.

In-vitro Experiment 1

This experment was performed by culturing the hybrid gel containing insulin-producing cells, to which mutant insulin gene encoding proinsulin susceptible to furin was introduced, and measured levels of IRI secreted into the culture medium.

1) Materials

Two types of skin-derived cell lines were used.
(1) Rat skin fibroblasts with mutant insulin gene being convertible with furin (RSFinsfur).
(2) RSK RSFinsfur were prepared by introducing mutant insulin gene (D. J. Groakreutz et al, The Journal of Biological Chpmistry, 269 (8), 6241, 1994), capable of processing by furin (insulins occur when the proinsulin chains are cleaved at two portions), to the fibroblasts (RSF) obtained from rat skin by primary culture. The gene was transducted into RSF using plasmid expressiom vectors pRIS-proins-Ifur-IIfur-B10D which contained the above-mentioned mutant insulin gene, according to the same method described in Example 1. The vector-transducted cells were then selectively increased in culture medium containing G418 of 800 μg/ml concentration.

Thirty-two clones were isolated from these cells and the clone of the highest IRI value were selected. This clone (RSFinsfur) secreted 24.5 μIU/hour IRI per $10^6$ cells in the culture medium.

These cells simultaneously expressed processing enzyme, furin for conversion of insulin, and thus proinsulin, precursor of insulin, was converted into insulin depending on the furin activity of the cells.

The RSFinsfur cells were immunohistologically studied using anti-furin monoclonal antibody (Genentech, South San Francisco,Calif.) and anti-insulin rabbit serum (Austral Biological, San Ramon, Calif.). The results are shown in Table 7. It was confirmed immunohistologically that these cells produce insulins and furin.

TABLE 7

| Type of Antibody | Result of staining |
|---|---|
| Anti-furin monoclonal antibody | Positive |
| Anti-insulin rabbit serum | Positive |

2) Culture Medium

Culture media A and B used in Example 1 were used for RSFinsfur and RSK, respectively Culture medium A was used after the cells were enclosed in and lamimated on the gel.

3) Procedures

Gel G was prepared by enclosing 3×$10^6$ cells of RSFinsfur in the gel which was then laminated RSK cells of the same number. The structure of Gel G is summarized in Table 8. Gel G was cultured at 37° C. in a 6 ml culture medium. The culture medium was replaced with new one every other day. The Gel on the 8th day of culture was rinsed with culture medium three times, and the culture medium was replaced with new one. The Gel was further cultured for 8 hours. The IRI value of the culture medium was measured with the insulin EIA.

TABLE 8

| Gel | Cells in the gel | Cells on the gel |
|---|---|---|
| Gel G | RSFinsfur (N = 3 × $10^6$) | RSK (N = 3 × $10^6$) |

4) Results

The results of this experiment confirmed that Gel G secreted 25.2 μIU IRI in eight hours. The Gel G secretes stable insulin for many hours, and thus, insulin can be delivered into the body when the Gel is transplanted to the skin.

In-vitro Experiment 2

This experiment was performed to examine a method to increase secretion of insulin from the hybrid gel containing insulin-producing cells, to which mutant insulin gene encoding proinsulin susceptible to furin was introduced.

1) Materials

The same cells as used in the above in-vitro experiment were used.

2) Culture Medium

The same culture media as used in the above in-vitro experiment were used in the same manner.

3) Procedures

Gel H was prepared by enclosing $10^6$ cells of RSFinsfur in the gel, which was then laminated with RSK cells of the sane number. Gels I and J were prepared by introducing polyglycolic acid (PGA) meshes (Davis+Geck, Manati, PR) cut to a circular form of 15 cm and 25 cm in diameter, respectively, into the gels simultaneously with the enclosure of RSFinsfur cells of the same number. The gel was then laminated with RSK. The structure of these Gels is shown in Table 9.

TABLE 9

| Gel | Cells in the gel | Material in the gel | Cells on the gel |
| --- | --- | --- | --- |
| Gel H | RSFinsfur (N = 10$^6$) | None | RSK (N = 10$^6$) |
| Gel I | RSFinsfur (N = 10$^6$) | PGA mesh 15 mm in dia. | RSK (N = 10$^6$) |
| Gel J | RSFinsfur (N = 10$^6$) | PGA mesh 25 mm in dia. | RSK (N = 10$^6$) |

These Gels were cultured at 37° C. in a 2 ml culture medium, respectively. Culture medium was replaced with new one every or every other day. The Gels were rinsed three times on the 8th day of culture with a culture medium, and the culture medium was replaced with new one. The Gels were further cultured for 8 hours in the new medium. A small quantity (50 µl) of culture medium was sampled during the period to measure the IRI value in the culture medium with insulin EIA.

4) Results

The results of this experiment are shown in Table 10. The Gels I and J containing both meshes and cells and further laminated with RSK cells secreted a significantly greater quantity of insulin than Gel H which contained only cells in and on the gel. It is thus confirmed that the presence of mesh in the gel is effective for increasing the secretion of insulin from the cells.

TABLE 10

Secretion of insulin from Gels to culture medium

| | Cumulative IRI value (uIU/gel) | | | |
| --- | --- | --- | --- | --- |
| | 1 hour | 2 hours | 4 hours | 8 hours |
| Gel H | 0.8 | 2.4 | 4.1 | 7.5 |
| (N = 4) | 1.6 | 3.3 | 3.5 | 6.7 |
| | 1.6 | 2.5 | 3.5 | 5.0 |
| | 0.8 | 0.8 | 4.1 | 4.1 |
| Gel I | 8.4 | 8.4 | 21.9 | 37.1 |
| Gel J | 9.3 | 15.4 | 30.3 | 47.6 |

In-vivo Experiment

Insulin producing cell-enclosed gel was transplanted to model diabetic animals to evaluate effects of the hybrid gel transplantation by measuring the weight and blood sugar level of the animals.

1) Experiment Animals 200 mg/kg of streptozotocin was intraperitoneally administered to the Balb/c nude mice (7-week old, male) at twice in two days to induce the high blood sugar condition. The experiment was started after confirming that the mice showed a high blood sugar levels.

2) Materials

Three types of rat skin-derived cell lines were used.
(1) RSF
(2) RSFinsfur
(3) RSK 3) Method for Preparing Gels (Artificial Skin)

RSFinsfur cells of 3×10$^6$ were enclosed in collagen gel and RSK cells of the same number were laminated on the surface of said gel to prepare Gel K. 3×10$^6$ cells of RSF were enclosed in collagen gel and RSK cells of the same number were laminated on the surface of said gel to prepare Gel L. The structure of these Gels is summarized in Table 11.

TABLE 11

| Gel | Cells in the gel | Cells on the gel |
| --- | --- | --- |
| Gel K | RSFinsfur (N = 3 × 10$^6$) | RSK (N = 3 × 10$^6$) |
| Gel L | RSF (N = 3 × 10$^6$) | RSK (N = 3 × 10$^6$) |

4) Procedures

The skin at the back of the model diabetic animals was cut away in the form of a circle of approximately 11 mm in diameter, and Gel K, cultured for 8 days after preparation and contracted to approximately 10 mm in diameter, was transplanted to the naked area on the animals. Gel L with cells not transduced with gene was transplanted in the same manner for control. After transplantation, the weight of the animals was measured and approximately 5 µl blood was sampled from the tail every other day to measure blood sugar level using Gultest-E.

5) Results

The results of this experiment are shown in Table 12. The control animals (Gel L transplanted group) show a decrease in the weight and increase in the blood sugar level while three was a tendency that increase in the weight and decrease in the blood sugar level were observed for Gel K (containing mutant insulin gene-transduced cells) transplanted group. This confirms improvements in the diabetic symptoms.

TABLE 12

Effects of Gel transplantatin to diabetic mouse

| Days after transplantation | 0 | 2 | 4 | 6 | 7 | 8 |
| --- | --- | --- | --- | --- | --- | --- |
| Treated group (Gel K group) | 19.6 | 18.2 | 18.4 | 19.7 | 19.6 | 19.6 |
| | 181 | 119 | 126 | 230 | 335 | 288 |
| Control group (Gel L group) | 19.8 | 17.5 | 18.0 | 18.0 | 18.1 | 17.8 |
| | 152 | 104 | 112 | 236 | 231 | 278 |
| | 21.4 | 18.0 | 18.2 | 17.9 | 17.6 | 18.3 |
| | 263 | 119 | 229 | 428 | 426 | 500 |

| Days after transplantation | 9 | 10 | 11 | 12 | 13 |
| --- | --- | --- | --- | --- | --- |
| Treated group (Gel K group) | 20.1 | 20.1 | 21.0 | 22.0 | 22.2 |
| | 362 | 238 | 312 | 333 | 380 |
| Control group (Gel L group) | 18.4 | 19.0 | 19.1 | 19.5 | 19.6 |
| | 316 | 326 | 286 | 334 | 468 |
| | 17.4 | 17.4 | 18.0 | 18.3 | 18.3 |
| | 405 | 393 | 352 | 397 | 641 |

Note)
Body weight: upper
Blood insulin level: lower

What is claimed is:

1. An artificial skin secreting human proinsulin, human insulin, or both human proinsulin and insulin, which consists essentially of (1) a mixture of biopolymer gel and skin fibroblasts and (2) skin epidermal cells overlaid on the mixture of biopolymer gel and skin fibroblasts, wherein said epidermal cells or both said skin fibroblasts and said epidermal cells are transformed with a recombinant expression vector comprising a DNA sequence expressing human proinsulin or human insulin, or both human proinsulin and insulin.

2. The artificial skin according to claim 1, wherein the number of said skin fibroblasts and the number of said epidermal cells are substantially the same.

3. The artificial skin according to claim 1, wherein the number of transformed skin fibroblasts and epidermal cells and the number of non-transformed skin fibroblasts and epidermal cells are substantially the same.

4. The artificial skin according to claim 1, wherein the mixture of biopolymer gel and skin fibroblasts further comprises a mesh material or porous membrane.

5. The artificial skin according to claim 1, wherein the recombinant expression vector is pBMG-neo-ins which expresses human proinsulin.

6. A method for treating diabetes, which comprises transplanting the artificial skin of any one of claims 5 and 1–4 onto the skin of a patient wherein the transplanted artificial skin secretes human proinsulin, human insulin or both human proinsulin and insulin in an amount effective to reduce the blood sugar level of the diabetic patient.

7. The artificial skin according to claim 1, wherein the number of transformed skin epidermal cells and the number of non-transformed skin epidermal cells are substantially the same.

* * * * *